United States Patent [19]

Cerola et al.

[11] Patent Number: 5,303,735
[45] Date of Patent: Apr. 19, 1994

[54] VALVE ASSEMBLY

[75] Inventors: Joseph J. Cerola; Richard M. Davis; Rowland W. Kanner, all of Guntersville, Ala.

[73] Assignee: Ryder International Corporation, Arab, Ala.

[21] Appl. No.: 802,309

[22] Filed: Dec. 4, 1991

[51] Int. Cl.⁵ .............................................. F16K 11/22
[52] U.S. Cl. .................................. 137/596.2; 251/205; 251/229; 251/297; 251/252; 251/285
[58] Field of Search ............... 251/205, 229, 289, 297, 251/252, 253, 263; 137/596.2

[56] References Cited

U.S. PATENT DOCUMENTS

| | | | |
|---|---|---|---|
| 1,740,602 | 12/1929 | Keeler | 251/289 X |
| 2,977,087 | 3/1961 | Lindgren et al. | 251/289 X |
| 3,122,350 | 2/1964 | Reeder | 251/289 X |
| 4,156,519 | 5/1979 | Janz et al. | 251/205 X |
| 4,552,336 | 11/1985 | Pastrone | 251/205 X |
| 4,664,139 | 5/1987 | Pfeiffer | 251/205 X |

Primary Examiner—Arnold Rosenthal
Attorney, Agent, or Firm—Trexler, Bushnell, Giangiorgi & Blackstone, Ltd.

[57] ABSTRACT

A valve assembly includes a housing having at least one valve orifice for fluid flow therethrough, and a valve member which moves between a fully closed position and a fully open position, respectively, closing and opening said valve orifice. The valve orifice has a clearance surface forming an auxiliary valve passageway selectively enabling flow communication therethrough in an intermediate position of the valve member between said fully open and fully closed positions, and in the intermediate position the valve member partially obstructs the valve orifice so that the passageway provides attenuated fluid flow communication through the valve orifice relative to fluid flow communication in the fully open position of the valve member. A manually controlled actuator enables limited displacement of the valve member between the fully closed position and the intermediate position for the attenuated flow communication through the valve orifice. The valve assembly can be one of dual valves for particular use as a surgical trumpet valve assembly housed within a two-part housing.

14 Claims, 2 Drawing Sheets

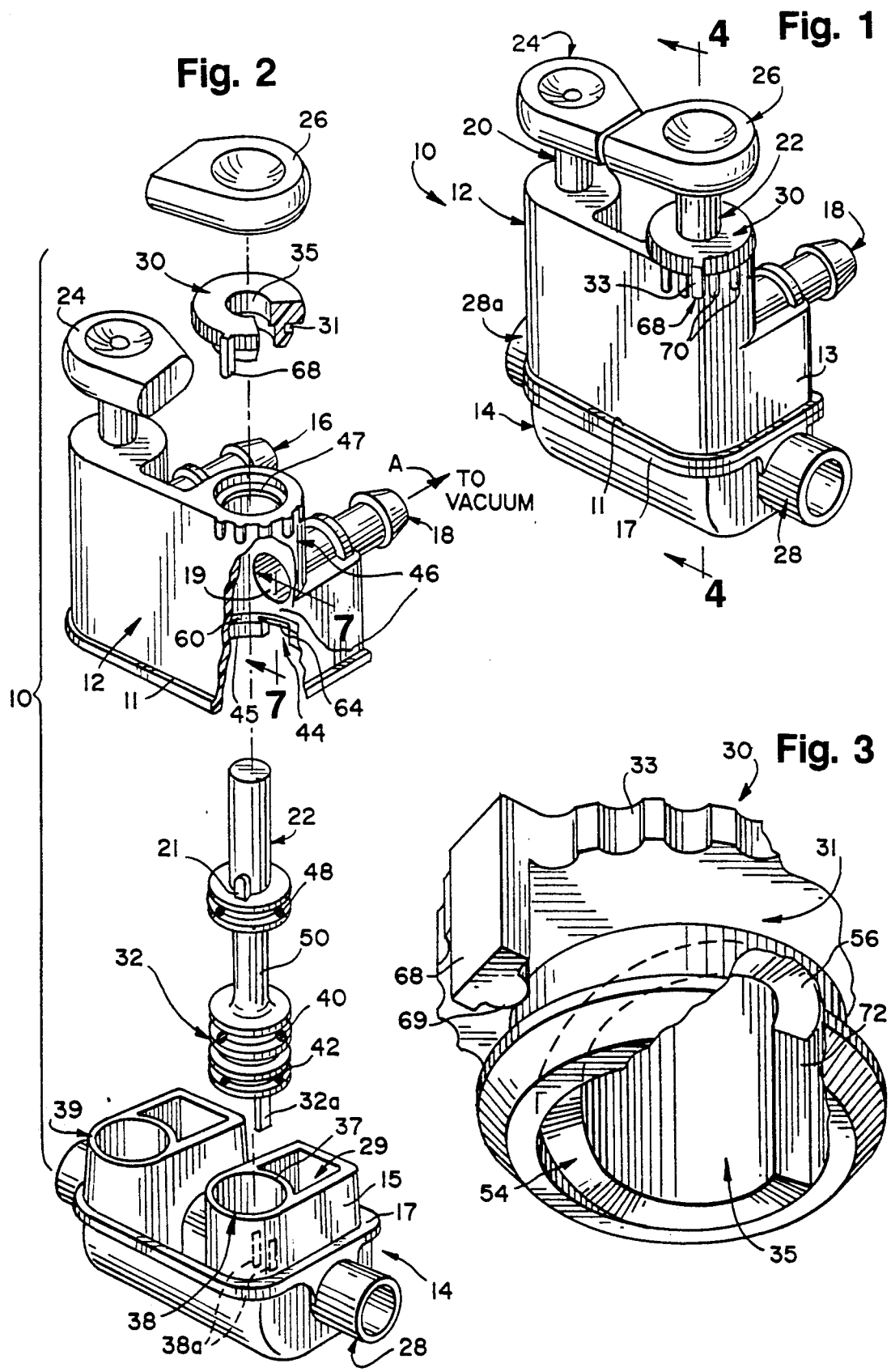

VALVE ASSEMBLY

BACKGROUND OF THE INVENTION

This invention relates to valve assemblies, and more particularly relates to improved valve structures for fluid delivery systems employed in surgical procedures.

Laparoscopic surgical procedures have been improved by endoscopic direction of laser surgery resulting in reduced complication and risk of infection. For example, laser surgery on a gallbladder is accomplished by inflation of the cavity with a controlled flow rate of $CO_2$ while the surgeon endoscopically directs the laser surgery on the target tissue. In addition, the target site is irrigated with pressurized irrigation solution followed by vacuum aspiration. The surgeon controls the irrigation and vacuum aspiration using a dual valve assembly referred to as a "trumpet valve" in which the valved irrigation and vacuum lines are independently controlled by digital manipulation within a commonly housed module held by the surgeon. However, the target tissue vaporized by the laser produces a smoke-like "laser plume" which can could the surgeon's vision through the endoscope, requiring that the clouding vapor be periodically removed by vacuum aspiration through the trumpet valve. The interrupting removal of the clouding vaporized tissue by the vacuum aspiration requires a difficult valve control which must regulate the vacuum flow rate at a level which will not adversely aspirate the $CO_2$ pressure necessary to prevent deflation of the cavity. This valving control problem is eliminated by the improved valve structure according to the present invention.

SUMMARY OF THE INVENTION

In accordance with the present invention, the valve assembly includes a housing having at least one valve orifice for fluid flow therethrough, and a valve member which moves between a fully closed position and a fully open position, respectively, closing and opening said valve orifice. The valve orifice has a clearance surface forming an auxiliary valve passageway selectively enabling flow communication therethrough in an intermediate position of the valve member between said fully open and fully closed positions, and in the intermediate position the valve member partially obstructs the valve orifice so that the passageway provides attenuated fluid flow communication through the valve orifice relative to fluid flow communication in the fully open position of the valve member. A manually controlled actuator enables limited displacement of the valve member between the fully closed position and the intermediate position for the attenuated flow communication through the valve orifice.

In preferred embodiment, the auxiliary valve passageway is provided by a chamfer formed at a peripheral surface of the valve orifice which enables a continuous gradient in dimension of the flow clearance between the chamfer surface and the range of valve member displacements within the intermediate position, providing a controlled variation in the attenuated fluid flow communication. The actuator control includes a thumbwheel which rotates a cam structure and propels the limited range of valve member displacements creating the continuous gradient in dimension of the auxiliary valve passageway. The resulting controlled attenuation in vacuum suction through the valve for example to aspirate surgical laser-vaporized tissue cloud without fully opening the valve or excessively withdrawing $CO_2$ prevents jeopardizing the pressure necessary to maintain inflation of the cavity. The valve assembly can be one of dual valves for particular use as a surgical trumpet valve assembly housed within a two-part housing for another aspect in accordance with the invention. The two-part housing includes an upper housing portion integrally including a pair of separate conduits for connection to respective fluid supply lines such as pressurized irrigation solution and vacuum aspiration. Each of the conduits in the upper housing portion has an internal opening into a respective cylindrical bore through which a valve element can be sealingly reciprocated. The lower housing portion of the two-part housing integrally includes a pair of separate cylindrical bores arranged for aligned extension from the respective upper cylindrical bores in the upper housing portion, and a common, manifold conduit from which a pair of separate passageways provide flow communication. Separate valve orifices are internally formed through at least one of the upper or lower housing portions and the valve orifices are arranged to provide respective flow communication between one of the passageways and one of the cylinder bores, so that each of the reciprocating valve elements within the respective cylinder bore controls fluid flow through the respective valve orifice to or from the manifold conduit. The two-part housing facilitates molding in that intersecting molding cores are not required to fabricate the connecting passageways.

BRIEF DESCRIPTION OF THE DRAWINGS

FIG. 1 is a perspective view of an embodiment of the valve assembly according to the invention;

FIG. 2 is an exploded, perspective view of the valve assembly shown in FIG. 1;

FIG. 3 is a partially fragmentary, enlarged view of the thumbwheel actuator for attenuated valving, shown in FIGS. 1 and 2;

DETAILED DESCRIPTION OF THE INVENTION

Figure 4:
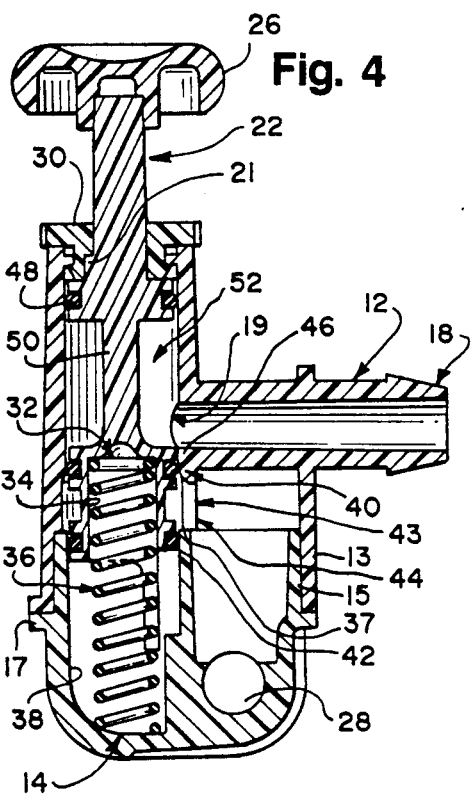
FIG. 4 is a sectional view along a plane indicated by line 4—4, indicating a fully closed position of the illustrated valve.

Referring to FIGS. 1 and 2, an embodiment of an improved trumpet valve assembly according to the present invention is designated generally by reference character 10. The valve assembly 10 has upper and lower housing portions designated 12 and 14, respectively. The two-portion housing construction facilitates both assembly of the valving and molding of the housing particularly in that intersecting molding cores are not required to fabricate the connecting passageways, which will be appreciated following the description hereinafter.

The upper housing 12 is molded to include two supply conduit connectors 16 and 18. When the trumpet valve assembly 10 is employed for fluid system control in a laparoscopic surgical procedure, the conduit 16 is connected to a conventional irrigating solution pump and the conduit 18 is connected to an aspirating vacuum pump (neither pump shown). The irrigation supply through conduit connector 16 and the vacuum aspiration through conduit connector 18 are independently controlled by separate valves with respective reciprocating valve stems 20 and 22 which are manually depressed from buttons 24 and 26. The valves, as described hereinafter, control independent flow communication of the conduits 16 and 18 with a common manifold conduit 28 formed in the lower housing portion 14 which is connectable to one or more flow lines (not shown) leading to the surgical site. The manifold conduit 28 has a second, linearly aligned access opening 28a which can also enable a passageway through the conduit 28 for additional surgical instruments (not shown) in known manner.

Figure 6:
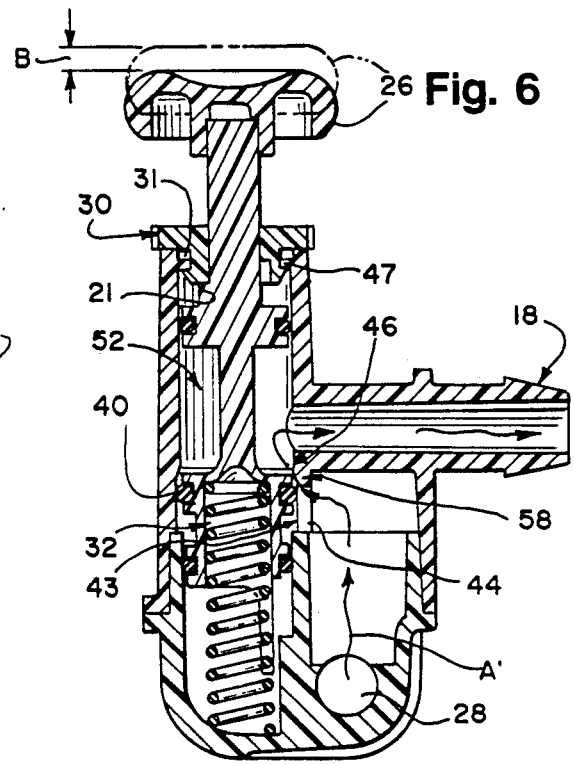
FIG. 6 is a view similar to FIGS. 4 and 5, illustrating an intermediate, flow attenuation position of the valve.
Figure 5:
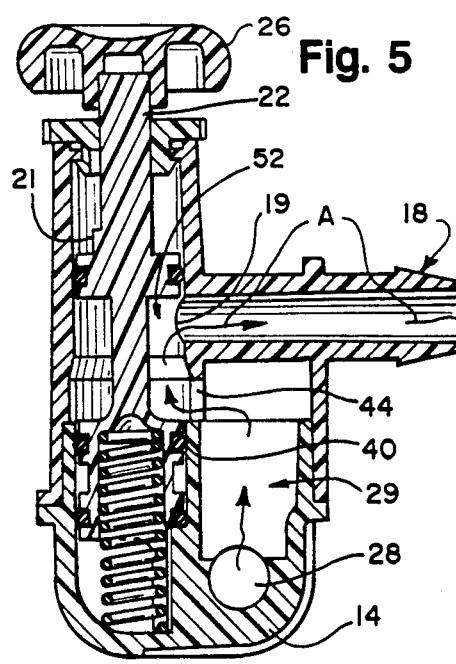
FIG. 5 is a view similar to FIG. 4 illustrating a fully closed position of the valve.

Each of the valve stems 20 and 22 can be identical and the valves operate in similar manner with the important exception that in the configuration illustrated, an additional auxiliary valve control operated by a rotatable thumb wheel actuator 30 is included on only one of the valves 43 (FIGS. 4-6) operated by the valve stem 22, so that the following description focuses primarily on this valve which would normally control the vacuum line through conduit 18 as shown in FIGS. 4-6.

Referring again to FIG. 2, each of the valve stems 20 and 22 has a lower portion forming a spool-type valve element 32 as shown on the valve stem 22. As best shown in FIG. 4, the annular valve element 32 has a central bore 34 which accepts the upper portion of a coil spring represented at 36 which is supported within the valve cylinder 38 formed in the bottom housing portion 14. Similar cylinder 39 is provided for the valve element (not shown) on the valve stem 20 for the other valve controlling the flow through conduit 16, typically for controlling inflow of irrigation solution. As shown in FIG. 4, the spring 36 upwardly biases the valve element 32 and stem 22 into top dead-center position in which upper and lower 0-rings 40 and 42 on the valve element 32 straddle the valve orifice 44 and each seal against respective cylinder walls 46 and 38, to form the closed position of the valve generally designated 43.

As best shown in FIG. 2, the valve orifice 44 is formed as a generally rectangular aperture through the valve cylinder wall 46 and extends to interrupt the bottom edge 45 thereof. The upper edge 37 of the lower valve cylinder wall 38 forms the bottom periphery of the rectangular valve orifice 44 in the assembled valve 10 as best shown in FIG. 4.

The cylinder wall 38 in the lower housing portion 14 forms an extension of the cylinder wall 46 in the upper housing portion 12 which thus cooperate to provide a continuous bore through which the valve member 32 reciprocates with the valve stem 22. After inserting the spring valve stems 20 and 22, the upper housing 12 is assembled on the lower housing 14 by welding the circumscribing overlap of the respective upper peripheral wall 13 on the lower peripheral wall 15 and respective mating circumferential shoulders 11 and 17 as best shown in FIG. 1.

Referring again to FIGS. 2 and 4, the upper portion of the valve stem 22 seats on O-ring 48 which provides a sliding seal against the upper cylinder wall 46. Between the O-ring 48 and the O-ring 40 is a reduced-diameter stem portion 50 which creates an annular clearance recess 52 which is always in flow communication with the interior opening 19 from the vacuum conduit 18 as reflected in the operating positions of the valve 43 illustrated in each of FIGS. 4-6.

Referring to FIG. 4, the valve 43 is closed by the biasing spring 36, as aforementioned, for example when the other valve stem 20 and corresponding valve is opened to deliver a pressurized irrigation solution from the conduit 16 through the manifold 28 leading to the surgical target site. Subsequently, for example, when the surgeon wishes to aspirate the irrigation solution from the cavity of the target site, the valve 43 would be fully opened as shown in FIG. 5 (after closing the other valve from line 16) by depressing the button 26 and valve stem 22 so that the O-ring 40 is downwardly displaced entirely below the valve orifice 44 which enables flow communication between the valve orifice 44 and the annular clearance 52 and vacuum opening 19 so that the irrigation solution can be reversed in flow from the surgical cavity by aspiration into the manifold 28 and vestibule chamber 29 leading to the valve orifice 44 along the aspiration flow path A leading to the vacuum or suction pump.

In order to enable only a small partial opening of the valve 43 which is very difficult to establish reliably by simple depression of the button 26 and valve stem 22, for example when the vaporized tissue or "laser plume" clouds the surgeon's endoscopic vision within the cavity, and particularly the surgical target site, a precisely controlled level of attenuated flow communication through the valve 43 is achieved by manual rotation of the thumbwheel-actuator 30 which is rotationally secured on the top of the valve cylinder 46 and through which the valve stem 22 reciprocates. Referring particularly to FIGS. 2 and 6, the top of the valve cylinder wall 46 has an internally projecting annular flange 47 which is snap-fitted into an annular groove 31 located below the knurled, gripping portion 33 on the top of the actuator 30. As best shown in FIG. 31, the lower portion of the central bore 35, through which the valve stem 22 extends, is surrounded by an internally formed spiral ramp generally designated by reference character 54 which serves as a rotating cam which rides against a cam-following element 21 radially projecting from the upper portion of the valve stem 22 as best shown in FIG. 2.

In the initial, fully closed position of the valve 43, as shown in FIG. 4, the highest elevation point 56 of the spiral ramp 54 is engaged above the cam-following element 21 allowing the valve stem 22 to be maintained in the biased closure position. As the thumbwheel-actuator 30 is rotated, the corresponding rotation of the spiral ramp 54 gradually forces the cam-following projection 21 and the stem 22 downwardly in a smoothly continuous gradient of lowering motion against the bias of the spring 36, limited by the degree of rotation of the actuator 30. The cam-following projection 21 and stem 22 are prevented from rotating by a vertical guide arm 32a extending downwardly from the valve member 32, which vertically rides between two vertical guide ribs 38a extending integrally from the lower cylinder wall 38. The resulting small differential lowering of the stem 22 correspondingly lowers the O-ring 40 by the same differential displacement, which is indicated as B, representing the differential lowering of the button 26 between the position in FIG. 4 and the position in FIG. 6. The same corresponding displacement B moves center of the O-ring 40 between the corresponding positions relative to the stationary upper cylinder wall 46 against which the O-ring 40 indicated in the dashed line in FIG.

Figure 7:
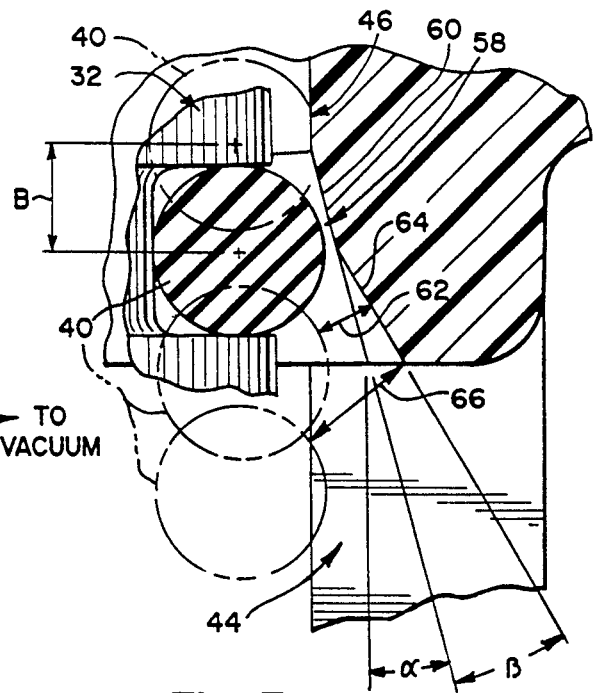
FIG. 7 is a fragmentary, enlarged view of the valve in the position shown in FIG. 6.

7 seals as previously shown in the closed position of the valve 43 in FIG. 4. As a result of the lowered displacement B of the O-ring 40 produced by the camming action of the actuator 30 rotation, a small clearance passageway 58 is created between the displaced O-ring 40 and the radially outwardly chamfered edge 60 adjacent the cylinder wall 46 which forms an entrance or clearance surface to the valve aperture 44. To facilitate molding, the chamfer 60 is annularly formed as part of the cylinder wall 46 as shown in FIG. 2, and is inclined at an angle alpha relative to the vertical reference as indicated in FIG. 7. The passageway 58 provides an attenuated, auxiliary opening or "bleed" portion of a fluid flow path through the valve 43 as part of the flow path designated A' as shown in FIG. 6 in an intermediate position of the valve member 32 between the fully closed position of the valve 43 shown in FIG. 4 and the fully open valve position shown in FIG. 5.

As the actuator 30 and spiral ramp 54 are further rotated, the resulting additional differential lowering of the valve member 32 and O-ring 40 creates a progressively wider passageway gap 62 between the O-ring 40 and the secondary chamfer 64 which extends radially outwardly from the chamfer 60 at the top of the valve orifice 44 as also shown in FIG. 2. The chamfer 64 is inclined at an additional angle Alpha plus Beta relative to vertical, each of which may be for example approximately 15° to create the auxiliary, or "bleed" clearance passageway. Thus, variable rotation of the actuator 30 and spiral ramp cam enables controlled variation in the attenuated fluid flow communication represented by the increasing dimension of the gaps 58, 62 and 66 corresponding to the continuous range of small, intermediate displacements of the valve member 32. In order to enable the surgeon to conveniently maintain a constant level of attenuated vacuum aspiration along the flow path A' as shown in FIG. 6, the thumbwheel portion 33 of the actuator 30 has a peripheral, downwardly extending indicator arm 68 and detent 69 on the backside thereof which produces an interference fit between adjacent detents 70 in an arcuate series thereof which radially extend from the exterior of the top of the valve cylinder 46 as shown in FIGS. 1 and 2. The interference fit of the detent 69 between successive pairs of detents 70 not only retains the thumbwheel 33 and actuator 30 at increments of rotation, but in addition, the indicator 68 also provides the surgeon with a monitor of the cumulative rotation of the actuator 30 corresponding to the progressive level of the attenuated vacuum aspiration achieved through the valve 43. The interference fit of the detent 69 and detents 70 is sufficient to maintain each increment of actuator rotation and overcome the upward bias of the spring 36 on the valve element 32.

Referring to FIG. 3, the vertical wall 72 below the highest point 56 on the spiral 54 serves as a stop against the cam-following element 21 on the valve stem 22 to establish the maximum degree of rotation of the actuator 30 corresponding to the maximum level of attenuation or "bleed" of the vacuum aspiration through the valve 43, for example a maximum flow rate of five liters per minute, so that $CO_2$ is not excessively aspirated through the valve 43 avoiding any interference with the proper inflation of the organ cavity. When the vacuum bleed is to be discontinued, the surgeon need only reverse the rotation of the actuator 30 resulting in the biased elevation of the valve member 32 into the closed position of the valve 43 shown in FIG. 4; alternatively, if a surgeon wishes to proceed with substantially maximum aspiration through the valve 43, he need only depress the button 26 to fully open the valve in the position shown in FIG. 5 as the valve stem 22 passes through the actuator 30 without interference.

While particular embodiments of the present invention have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

The invention is claimed as follows:

1. A valve assembly comprising: a housing including at least one valve orifice for fluid flow therethrough, a valve member which moves between a fully closed position and fully open position respectively closing and opening said valve orifice, control means for selectively limiting displacement of said valve member between said fully closed position and an intermediate position of said valve member, said intermediate position of said valve member partially obstructing said valve orifice to provide attenuated fluid flow communication through said valve orifice relative to fluid flow communication in said fully open position of said valve member, wherein said control means comprises a manually movable actuator projecting from said housing for said limiting displacement of said valve member and further comprises detent means extending from said housing for releasable interference preventing motion of said actuator and for maintaining said intermediate position of said valve member.

2. A valve assembly according to claim 1, wherein said actuator is manually rotatable to attain said limiting displacement of said valve member.

3. A valve assembly according to claim 2, wherein said detent means releasably interferes with said actuator rotation.

4. A valve assembly according to claim 3, wherein said detent means comprises a plurality of spaced extensions from said housing for releasably maintaining said actuator in a variable series of sequential degrees of rotation corresponding to a controlled range of said valve member displacements and said attenuated fluid flow communication.

5. A valve assembly comprising: a housing including at least one valve orifice for fluid flow therethrough, a valve member movable between a fully closed position and fully open position respectively closing and opening said valve orifice, control means for selectively limiting displacement of said valve member between said fully closed position and an intermediate position of said valve member, said intermediate position of said valve member partially obstructing said valve orifice to provide attenuated fluid flow communication through said valve orifice relative to fluid flow communication in said fully open position of said valve member, said valve member comprising a valve stem which moves along a longitudinal axis thereof transversely across said valve orifice between said fully open and fully closed positions of said valve member, said valve stem including a recess extending only partially through said valve stem and providing a conduit and flow path extending to said valve orifice in said intermediate and fully open positions of said valve member.

6. A valve assembly comprising: a housing including at least one valve orifice for fluid flow therethrough, a valve member movable between a fully closed position and fully open position respectively closing and opening said valve orifice, control means for selectively limiting displacement of said valve member between said fully closed position and an intermediate position of said valve member, said intermediate position of said valve member partially obstructing said valve orifice to provide attenuated fluid flow communication through said valve orifice relative to fluid flow communication in said fully open position of said valve member, said valve member comprising a valve stem which moves along a longitudinal axis thereof transversely across said valve orifice between said fully open and fully closed positions of said valve member, said housing further comprising additional valve means for independent control of a separate fluid flow conduit, and a manifold conduit in flow communication both with said valve orifice and said additional valve means in order to enable flow through said manifold conduit of either of respective fluids controlled by said valve member and said additional valve means.

7. A valve assembly according to claim 5 wherein said valve orifice includes a clearance surface providing a metering passageway through said orifice in said intermediate position of said valve member to attenuate said fluid flow communication.

8. A surgical valve assembly including at least a pair of valve means for independently controlling fluids employed in a surgical procedure, wherein at least one of said valve means comprises first and second fluid flow conduits and a valve orifice arranged for controlling flow communication between said conduits; a valve plunger having a valve element movable between a fully closed position and fully open position respectively closing and opening said valve orifice; biasing means for urging said valve element toward said fully closed position; a movable actuator having cam means including an abutment surface against which a cam follower on the plunger is engaged in the closed position of the valve member; said actuator being selectively movable such that said cam means displaces said cam follower and plunger to urge said valve member to a selectable intermediate position, between said fully open and fully closed positions, partially obstructing said valve orifice and creating attenuated fluid flow communication through said valve orifice; and a manifold conduit in flow communication both with one of said first and second conduits and with the other of said valve means in order to provide flow through said manifold conduit of either of said respective fluids controlled by said pair of valve means.

9. A valve assembly according to claim 8 wherein said abutment surface has a ramp configuration and said cam follower slidably follows said ramp configuration during said motion of said actuator and valve member propulsion.

10. A valve assembly according to claim 9 wherein said ramp configuration has a spiral contour against which said cam followers slides to generate said valve member propulsion.

11. A valve assembly according to claim 8 wherein said valve orifice includes a clearance surface providing a metering passageway through said orifice in said intermediate position of said valve member to attenuate said fluid flow communication.

12. A valve assembly according to claim 11 wherein said valve orifice comprises an aperture transversely extending through an axially oriented bore within which said plunger moves in reciprocal motion.

13. A valve assembly according to claim 12 wherein said valve orifice includes a rectangular configuration and said clearance surface defines a peripheral edge of said rectangular configuration.

14. A valve assembly according to claim 11 wherein said valve plunger moves along a longitudinal axis thereof so that said valve element moves transversely across said valve orifice between said fully open and fully closed positions of said valve element.

* * * * *